United States Patent
Park et al.

(10) Patent No.: US 7,851,496 B2
(45) Date of Patent: Dec. 14, 2010

(54) IONIC LIQUID TYPE CROWN ETHER DERIVATIVES, METHOD FOR PREPARING THE SAME AND METHOD FOR ISOLATING METAL IONS USING THE SAME

(75) Inventors: Sang Hyun Park, Daejeon (KR); Seung Ho Jang, Daejeon (KR); Hui Jeong Gwon, Daejeon (KR); Myung Woo Byun, Daejeon (KR)

(73) Assignee: Korea Atomic Energy Research Institute, Daejon-Si (KR)

( * ) Notice: Subject to any disclaimer, the term of this patent is extended or adjusted under 35 U.S.C. 154(b) by 1147 days.

(21) Appl. No.: 11/473,751

(22) Filed: Jun. 23, 2006

(65) Prior Publication Data
US 2007/0173640 A1    Jul. 26, 2007

(30) Foreign Application Priority Data
Jan. 24, 2006    (KR)    .................... 10-2006-0007302

(51) Int. Cl.
*A61K 31/4188*    (2006.01)
*A61K 51/04*    (2006.01)
*C07D 273/00*    (2006.01)

(52) U.S. Cl. ........................ 514/397; 424/1.81; 540/467
(58) Field of Classification Search ................ 540/467; 514/397; 424/1.81
See application file for complete search history.

(56) References Cited

PUBLICATIONS

Donald J. Wood, et al., Separation of 90Y From 90Sr by Solvent . . . , Anal. Chem., vol. 65, pp. 1350-1354, 1993.*
Wan-Yu Lin, et al., Rhenium-188 Hydroxyethylidene Diphosphonate . . . , Euro. J. Nucl. Med., vol. 24, pp. 590-595, 1997.
V J Lewington, Cancer Therapy Using Bone-Seeking Isotopes, Phys. Med. Biol., vol. 41, pp. 2027-2042, 1996.
Kazuyuki Hashimoto, et al., Synthesis of 188 RE-MDP Complex . . . , Appl. Radiat. Isot., vol. 47, No. 2, pp. 195-199, 1996.
C. Cipriani, et al., Gamma Camera Imaging of Osseous . . . , Eur. J. Of Nucl. Med., vol. 24, pp. 1356-1361 1997.
I. Csete, et al., Standardization of 89SR at the National . . . , Applied Radiation and Isotopes, vol. 56, pp. 467-470, 2002.
Donald J. Wood, et al., Separation of 90Y From 90Sr by Solvent . . . , Anal. Chem., vol. 65, pp. 1350-1354, 1993.
S. Malja, et al., Preparation of 90Y by the 90Sr-90Y . . . , Journal of Radioanalytical and Nuclear Chemistry, vol. 245, No. 2, pp. 403-406, 2000.
C.J. Pedersen, Cyclic Polyethers and Their Complxes . . . , Journal of the American Chemical Society, vol. 89, pp. 7017-7036, 1967.
Andre Egli, et al., Organometallic 99mTc-Aquaion Labels Peptide . . . , The Journal of Nuclear Medicine, vol. 40, pp. 1913-1917, 1999.
Valerie J. Lewington, Targeted Radionuclide Therapy for Bone Metastases, Euro. J. Nucl. Med., vol. 20, pp. 66-74, 1993.
John D. Holbrey, et al., Ionic Liquid: Industrial Application For Green Chemistry, Amer. Chem. Soc., pp. 3-68, 2002.

* cited by examiner

*Primary Examiner*—Susannah Chung
*Assistant Examiner*—Janet L Coppins
(74) *Attorney, Agent, or Firm*—Lucas & Mercanti, LLP

(57) ABSTRACT

Disclosed relates to an ionic liquid type crown ether derivative, expressed by Chemical Formula 1 below, for isolating metal ions, a method for preparing the same and a method for isolating selectively the metal ions using the cycle size of the same. The present invention can provide the ionic liquid type crown ether and isolate metal ions including radioactive isotopes efficiently using the same. Furthermore, the prevent invention provides crown ether valuably used as a recyclable and environment-friendly isolating medium by preparing crown ether of ionic liquid type.

[Chemical Formula 1]

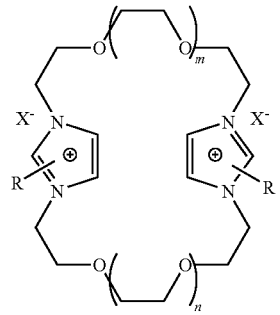

wherein m, n, $X^-$ and R are identical with those in the description.

10 Claims, No Drawings

IONIC LIQUID TYPE CROWN ETHER DERIVATIVES, METHOD FOR PREPARING THE SAME AND METHOD FOR ISOLATING METAL IONS USING THE SAME

This patent application claims the benefit of priority from Korean Patent Application No. 10-2006-0007302 filed Jan. 24, 2006, the contents of which are incorporated herein by reference.

BACKGROUND OF THE INVENTION

1. Field of the Invention

The present invention relates to ionic liquid type crown derivatives for isolating metal ions, a method for preparing the same and a method for selectively isolating metal ions using the same.

2. Description of Related Art

In general, nuclear medicine technologies for using nuclear power in medicine definitely require the use of a radiopharmaceutical. The radiopharmaceutical is prepared by selecting an appropriate material from among various kinds of radioactive isotopes generated when operating a nuclear reactor and processing it for use in the diagnosis or therapy of diseases to be administered to the human body. Such a radiopharmaceutical can readily and obviously detect metastasis of cancer that is difficult or impossible to diagnose using other techniques.

These days, extremely small quantities of radioactive isotopes have been applied to the nuclear medicine field. Some radioactive isotopes such as $^{89}$Sr, $^{186}$Re, $^{153}$Sm, $^{90}$Y and $^{166}$Ho have been used in typical methods of medical therapy. These therapeutic methods have been studied to prepare the radiopharmaceuticals that irradiate noxious cells at high levels and most rapidly and do not damage healthy cells.

The radiopharmaceuticals have been applied in the field of radiographic imaging techniques. That is, according to the radiographic imaging technique, after injecting small quantity of radiopharmaceutical such as technetium-99m in the body, the distribution labeled by such radiopharmaceutical is detected to find pathologic diseases or to assess the symptom degrees. The radiopharmaceutical used as a labeling substance is named as a contrast agent. The contrast agent comprising a radionuclide that emits radiation and a chelating agent coordinated with the radionuclide should satisfy the required conditions that it maximizes the detection efficiency of the radionuclide and minimizes the amount of radiation absorbed in a patient. Accordingly, technetium-99m and rhenium-188 have been generally used as radionuclides that emit γ-rays and have a physical half-life shorter than the imaging time (A. Egli, et al. The Journal of Nuclear medicine, 1999, 40, 1913; Wan-yu Lin, et al. European The Journal of Nuclear medicine, 1997, 24, 590; European The Journal of Nuclear medicine, 1993, 20, 66; V. J. Lewington. Physics in medicine and biology, 1996, 41, 2027; Kazuyuki Hashimoto, et al. Applied radiation and isotopes, 1996, 47, 195).

The radiopharmaceuticals are applicable to the diagnosis and therapy of cancers since the radiopharmaceuticals readily and obviously detect metastasis of cancers that is difficult or impossible to diagnose via other techniques. Skeletal metastasis occurring commonly in several cancers such as breast cancer, prostate cancer, lung cancer and kidney cancer is a major cause of death in patients who suffer from those cancers. So far, bone imaging techniques using technetium-99m have been known as a most selective and rapid way to find the skeletal metastases of cancer cells.

The radiations that the radioactive isotopes emit can be roughly classified into γ-ray, β-ray and α-ray. Each of the radiations has a different permeability according to its kind. The permeability that permeates a material relates to wavelengths. The wavelengths of the radiations become shorter in sequential order of α-ray, β-ray and γ-ray. Thus, γ-ray has the highest permeability. In general, radionuclides that emit γ-rays of high permeability have been used for diagnosis and therapy of cancers.

Meanwhile, methods of using radionuclides that emit β-rays will attract scientific attention in the future. So far, only $^{32}$P-phosphate and strontium dichloride ($^{89}$SrCl$_2$) therapies have been approved to applied to patients having tolerances to other anodynes among patients suffering from severe bone pains caused by such breast cancer, prostate cancer, lung cancer, kidney cancer, etc., accompanied with the skeletal metastases. In case of the cancers accompanied with the skeletal metastases, a small quantity of radiation should be distributed to the radiosensitive bone marrow and the minimum quantity of radiation be applied to cellular tissue adjacent to the marrow, whereas, a high dosage should be irradiated to bone surfaces where the skeletal metastasis occurs. Accordingly, e.g., the $^{89}$Sr that does not emit γ-rays permeating to the insides of cells but emits pure β-rays has been used.

The $^{89}$Sr has a half-life of 50.6 days and emits β-energy of 0.583 MeV from at an average distance of about 1.5 mm from the bone. Sr$^{2+}$ has the same pathway in the body as calcium and is attached to the mineral structure of the bone and, preferentially, to highly degenerated region such as metastasis damage region. A small amount of carrier-free $^{89}$Sr not attached among the $^{89}$Sr administered via 110 to 180 MBq of $^{89}$SrCl$_2$ in vivo injection is discharged from the body within 14 days, the biological half-life.

However, since $^{89}$Sr does not emit γ-rays, it is difficult to visualize directly the region affected with $^{89}$Sr. Especially, $^{89}$Sr has been used for imaging the metastasis region in vivo using a collimator and an appropriate gamma camera, although such method is inefficient that bremsstrahlung radiation is emitted from β-rays and it has a wide energy spectrum.

As described in detail above, $^{89}$Sr occupy an important position as a radioactive isotope for the bond imaging and, for this purpose, it is necessary to provide methods for isolating and extracting $^{89}$Sr (C. Cipriani, et al. European The Journal of Nuclear medicine, 1997, 24, 1356; I. Csete, et al. Applied Radiation and Isotopes, 2002, 56, 467).

In addition to $^{89}$Sr, $^{90}$Y that emits beta particles has attracted attention. $^{90}$Y is a radioactive isotope having $E_{\beta Max}$ of 2.3 MeV and $T_{1/2}$ of 64.1 h that does not emit γ-rays and is useful for therapy. Especially, $^{90}$Y has the properties of a half-life and a radioactive decay suitable for labeling a monoclonal antibody (Mab's) to be used for the therapeutic purpose of cancers. The $^{90}$Y is generated from $^{90}$Sr, a parent radionuclide, via the following radioactive decay process:

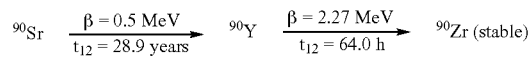

As shown in the decay process, the carrier-free $^{90}$Sr can be obtained continuously from the parent radionuclide $^{90}$Y theoretically. However, to prepare pure $^{90}$Y from a generator system, a high selectivity and a rapid isolation method are required. Especially, they are much required to apply the same to the nuclear medicine.

Meanwhile, in view of environmental samples, analyses of $^{90}Sr$ and $^{90}Y$ radioactive isotopes, the β-ray emitters, are very complicated as a matter of fact. Accordingly, it is necessary to chemically isolate the radioactive isotopes including $^{89}Sr$ prior to their application in the nuclear medicine field (J. Donald, et al. Analytical Chemistry, 1993, 65, 1350; S. Malja, et al. Journal of Radioanalytical and Nuclear Chemistry, 2000, 245, 403).

Meanwhile, macrocyclic polyethers have attracted attention recently as a method for isolating chemical species. For example, the following compounds are included in the macrocyclic polyethers and referred to as crown ethers because they have crown shapes.

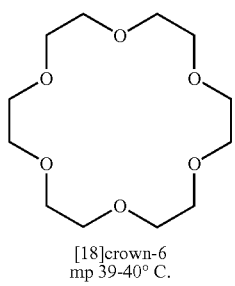

[18]crown-6
mp 39-40° C.

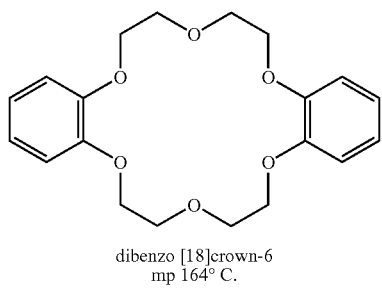

dibenzo [18]crown-6
mp 164° C.

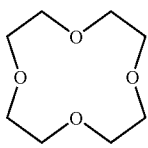

[12]crown-4
mp 16° C.

The first numerals of the compound names denote the number of atoms organizing a cycle, which expresses the size of the cycle. The second numerals of the compound names represent the number of oxygen out of the atoms organizing the cycle. The oxygen atoms are located generally between two carbon atoms.

The crown ethers have a characteristic that forms complexes with cations such as $Na^+$, $K^+$, etc. The cation enters selectively into the inside of the macrocyclic compound according to the sizes of cycle and cation. For example, as depicted in the following scheme, [18]crown-6 has a cavity diameter that is too broad for $Na^+$ of small size to be situated therein and too narrow for $Cs^+$ of large size to be settled therein. Accordingly, $K^+$ forms a snug fit. Meanwhile, [15] crown-5 is bound with $Na^+$ and [12]crown-4 is coupled with $Cs^+$.

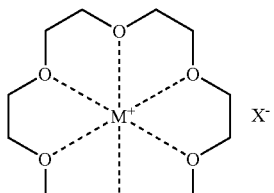

$M^+$ trapped in [18] crown-6

Cavity diameter 2.6-3.2 Å

Ion diameter $Na^+$ 1.90 Å
$K^+$ 2.66 Å
$Cs^+$ 3.34 Å only this ion forms a snug fit

Since the crown ether has a strong capability of forming a complex, with some quantity of crown ether, it is possible to dissolve even an ionic compound in an organic solvent. For example, potassium permanganate ($KmnO^4$) is not melted in benzene but well dissolved in water. However, if some quantity of dicyclohexyl [18]crown-6 is melted in benzene, the potassium permanganate dissolved in water can be extracted into benzene. The resultant "purple benzene" having permanganate ions, not eluted, is a strong oxidizer.

Recently, chiral crown ethers have been synthesized. These compounds coordinate with enantiomorphs of compounds satisfied with their chirality, but do not bond with the others. The chiral crown ethers are efficiently used for isolating racemic mixtures. In general, since enzymes have a capability for discriminating enantiomorphs, the chiral crown ethers have been studied as the form of enzymes.

Selective bondings of metal ions via the macrocyclic compounds occupy an important position in the natural world. For example, an antibiotic such as nonactin includes a macrocycle having oxygen atoms taking up fixed spaces. Nonactin, having four THF cycles bonded with four ester bonds, selectively bonds $K^+$ and $Na^+$ in water-soluble medium and carries $K^+$, not $Na^+$, via cell membrane (C. J. Pedersen, Journal of the American Chemical Society, 1967, 89, 7017).

Ionic liquid type crown ether (IL-CE) is composed of crown ether molecules, having the above-described features, introducing a functional group of ionic salts that execute a function of ionic liquid.

The ionic liquid denotes ionic salts that exist liquidly at 100° C. or less, like salt, differently from ionic salt compounds composed of metallic cations and nonmetallic anions melted at a high temperature of 800° C. or more. Especially, ionic liquid existing liquidly at room temperature is referred to as room temperature ionic liquid (RTIL). The ionic liquid is composed of organic cations and anions as shown in the following figure.

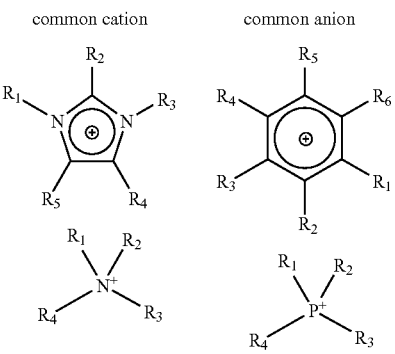
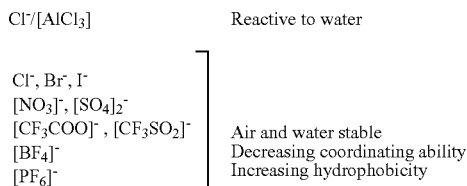

Since general organic solvent has a vapor pressure, the temperature for use of the organic solvent is limited and it is readily burnt out when it comes up close to fire. Besides, when introducing a specific structure to increase polarity, viscosity of the solution is increased due to interactions of molecules. However, the ionic liquid is a liquid having features of salt. Especially, the room temperature ionic liquid has a variety of features such as non-volatility, non-toxicity, non-combustibility, excellent heat-stability, ionic conductivity and the like. Furthermore, the room temperature ionic liquid having a high polarity dissolves inorganic and organometallic compounds well and exists liquidly at a wide range of temperature. Moreover, the room temperature ionic liquid has attractive features that it is a green reagent that is harmless to human being and is recyclable.

The ionic liquid having the above described various features can be applied in the intensive chemical fields as an enzyme for increasing the reaction rate, a green solvent that is recyclable after reaction, a medium for isolating and extracting a reaction product, applications in nano-chemistry, an electrolyte in electrical chemistry, a supercritical fluid and the like. Besides, according to the physicochemical properties of the ionic liquid, it is possible to readily synthesize an ionic liquid that coincides with a desired use since the ionic liquid can regulate the structures of cation and anions constituting the ionic liquid. Accordingly, the ionic liquid has been referred to as a designer solvent (Ionic liquids: Industrial application for green chemistry, American Chemical Society, 2002).

The above described crown ethers have limitations that it is difficult to synthesize such ethers by cycle sizes, they are of high cost and they are not recyclable. However, the ionic liquid type crown ethers have advantages that they can be readily synthesized using cheap starting materials via simplified organic synthetic methods and, especially, can be synthesized by cycle sizes. Besides, the ionic liquid type crown ethers can be used for selectively isolating and extracting a variety of metal ions since they have the same capability for selectively chelating metal ions according to cycle sizes as the crown ethers. Furthermore, the ionic liquid type crown ethers showing the features of the ionic liquid at the same time have a complete ionicity that is not provided by only the conversion of the functional group of crown ethers and have physical and chemical features different from the existing crown ethers, thus being used as a recyclable green reagent.

SUMMARY OF THE INVENTION

Accordingly, the inventors of the present invention have carried out researches aimed at finding a method for synthesizing ionic liquid type crown ethers (IL-CE) and a method for isolating and extracting radioactive isotopes or metal ions in high purities using the same and complete the present invention.

An object of the present invention is to provide ionic liquid type crown ethers.

Another object of the present invention is to provide a method for preparing the ionic liquid type crown ethers.

Still another object of the present invention is to provide a method for isolating and extracting metal ions using the ionic liquid type crown ethers prepared via the method.

To accomplish the above objects, the present invention provides ionic liquid type crown ether expressed by Chemical Formula 1 below.

[Chemical Formula 1]

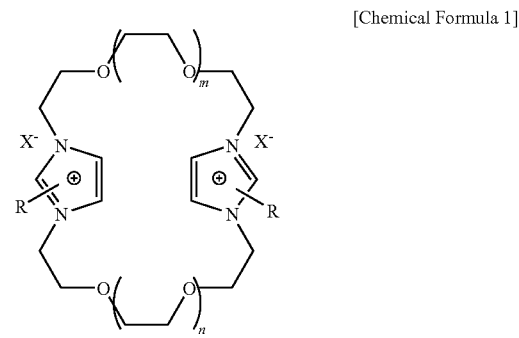

wherein m or n denotes positive numbers of 1 to 4, respectively;

$X^-$ represents an anion chemical species of ionic liquid; and

R expresses hydrogen or an alkyl group of $C_1$~$C_6$.

Hereinafter, detailed description of the present invention will be made.

In the ionic liquid type crown ether of Chemical Formula 1 in accordance with the present invention, the m or n denotes a cycle size. In case that the compound of Chemical Formula 1 has a symmetrical cycle based on an imidazole, m is the same as n. However, it is not necessary to keep the symmetry of the cycle. Accordingly, in this case, m is not the same as n.

The size of the cycle of the compound of Chemical Formula 1 can be varied suitable for the sizes of metal ions to be isolated, by regulating the m or n. In this case the m or n is desirably 1 to 4 and, preferably, 1 to 3. In case that the m or n is 5 or more, the cycle size becomes larger, which results in a failure to form a complex with metal ions.

In the ionic liquid type crown ether of Chemical Formula 1, the ionic species of ionic liquid expressed by $X^-$ may include Lewis base having a negative charge of dissociated strong acid or superacid, such as $AlCl_4^-$, $Al_2Cl_7^-$, $BF_4^-$, $PF_6^-$, $SbF_6^-$, $Cl^-$, $Br^-$, $I^-$, $NO_3^-$, $HSO_4^-$, $CF_3COO^-$, $CF_3SO_3^-$, $(CF_3SO_3)_2N^-$ and the like.

In the ionic liquid type crown ether of Chemical Formula 1, the R may be hydrogen or alkyls of $C_1$~$C_6$ and, desirably, R is alkyls of $C_1$~$C_3$. Preferably, R is hydrogen. If the size of a substitution group R is large and complicated, the R may obstruct the ionic liquid type crown ether in forming a complex with metal ions.

Furthermore, to accomplish the above objects, the present invention provides a method for preparing ionic liquid type crown ether expressed by Scheme 1 below. More particularly, the method for preparing ionic liquid type crown ether comprises: substituting alcohol groups of an ethyleneglycol compound 2 with $X^-$s to form a compound 3 [ST 1]; reacting the compound 3 prepared in ST 1 with substituted or non-substituted imidazoles 4 to prepare a compound 5 wherein the Xs of the compound 3 are substituted with the imidazole compounds 4 [ST 2]; and reacting the compound 5 prepared in ST 2 with a compound 6 to form a cyclic compound 1 expressed by Chemical Formula 1 in Scheme 1 below [ST 3].

The ethyleneglycol compound 2 having Chemical Formula 2 in Scheme 1 is used as a meaning that includes tri-, tetra-, penta-, hexa-ethyleneglycol, etc., wherein l is 3 or more.

-continued

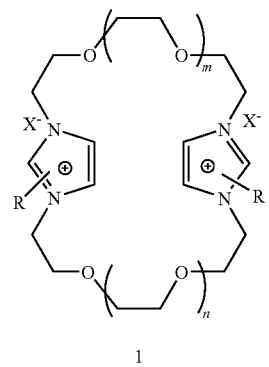

1 wherein m, n, $X^-$, and R are identical with those in Chemical Formula 1, and l denotes positive numbers of 3 to 6.

Furthermore, the present invention provides a method for preparing ionic liquid type crown ether further comprising: carrying out an anion exchange reaction with the ionic liquid type crown ether of Chemical Formula 1 of Scheme 1 prepared in ST 3 to prepare ionic liquid type crown ether having different physical properties and expressed by Chemical Formula 1' in Scheme 2 below [ST 4].

[Scheme 1]

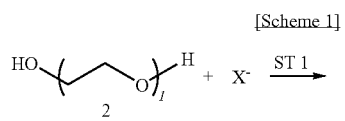

2

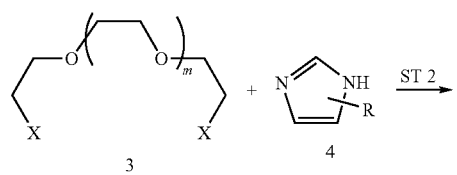

3    4

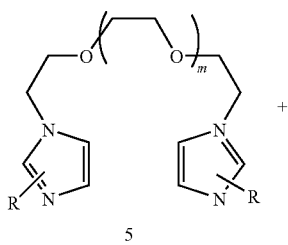

5

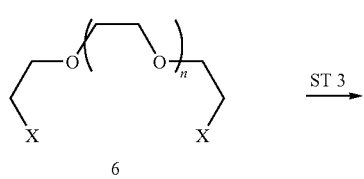

6

[Scheme 2]

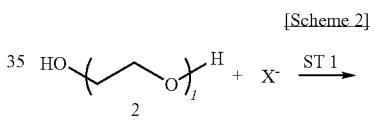

2

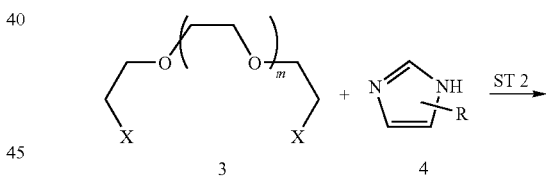

3    4

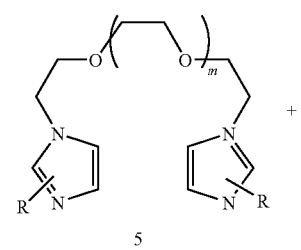

5

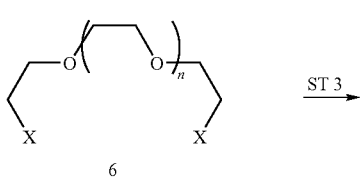

6

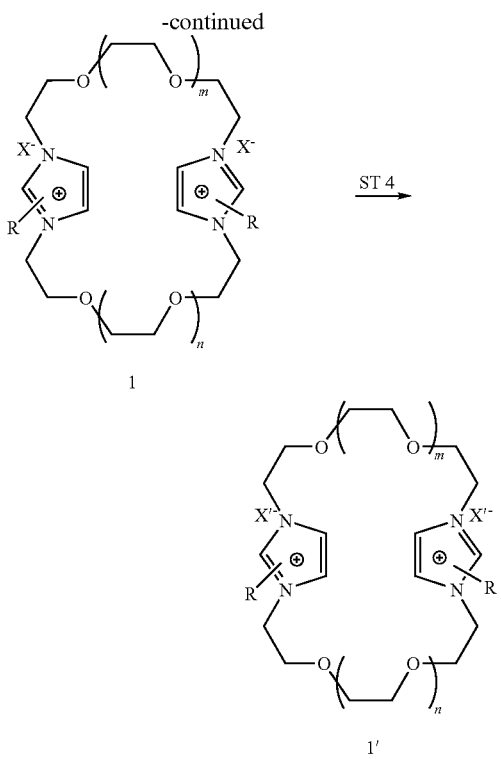

wherein m, n, X⁻, and R are identical with those in Chemical Formula 1, l denotes positive number of 3 to 6 and X'⁻ is Lewis base having a negative charge of dissociated strong acid or superacid, such as $AlCl_4^-$, $Al_2Cl_7^-$, $BF_4^-$, $PF_6^-$, $SbF_6^-$, $Cl^-$, $Br^-$, $I^-$, $NO_3^-$, $HSO_4^-$, $CF_3COO^-$, $CF_3SO_3^-$, $(CF_3SO_3^-)_2N^-$, etc.

In the method for preparing ionic liquid type crown ether of the present invention, ST 1 is the step of substituting alcohol groups located in the ends of the ethyleneglycol compound 2 with halogen atoms using Pederson method.

The Pederson method is to elongate the length of the cycle of ethyleneglycol compound 2, such as ethyleneglycol, triethyleneglycol, etc., for synthesizing various crown ethers, of which cycle sizes are subdivided, or to substitute the alcohol groups with halogen atoms for substitution and cyclization reaction of imidazole, thus preparing the compound 3.

To facilitate the substitution of the end alcohol groups of the ethyleneglycol compound 2, thionyl chloride ($SOCl_2$), phosphorus tribromide ($PBr_3$), or phosphorus triiodide ($PI_3$) is used, which, however, is not limited to any compounds that include halogen chemical species X⁻ of the ionic liquid and, at the same time, that are capable of substituting the alcohol groups.

Besides, it is desirable to use the ethyleneglycol compound 2 used in ST 1, in which l is 3 to 6. If the l is below 2, it is possible to form crown ethers. Meanwhile, if the l is above 7, the cycle sizes of the crown ethers are too large to form an effective complex with metal ions to be isolated.

In the method for preparing ionic liquid type crown ether of the present invention, ST 2 is the step of reacting the compound 3 prepared in ST 1 with substituted or non-substituted imidazoles 4 to prepare a compound 5 wherein the Xs of the compound 3 are substituted with the imidazole compounds 4.

In ST 2, the Xs of the compound 3 prepared in ST 1 are substituted and, in ST 3, the imidazole compounds 4 may be used to synthesize the ionic liquid type crown ethers of the invention by reacting with other compounds having the same or different cycle lengths as or from the compound 3.

The imidazole compound 4 can be used desirably since it provides two binding sites for the cyclization and the crown ether 1 formed after the cyclization is a cation chemical species constituting the ionic liquid and is converted into the form of imidazolium compound. That is, the imidazole compound 4 has unique features that cannot be expected in cation chemical species constituting the ionic liquid, such as alkylpyridinium, quaternary ammonium, quaternary phosphonium, etc., which results in desirable applications.

Furthermore, it is desirable to use hydrogen or alkyls of $C_1$ to $C_6$ as the substitution group R of the imidazole compound 4, preferably, hydrogen or alkyls of $C_1$ to $C_3$, and, most preferably, hydrogen. If the size of the substitution group R is large and complicated, the R may obstruct the ionic liquid type crown ether in forming a complex with metal ions.

In ST 2, it is desirable to react the compound 3 prepared in ST 1 with the imidazole compound 4 at room temperature for five to seven hours, after increasing nucleophilicity of the imidazole compound 4 under basic conditions.

Besides, the base is used for removing protons of the imidazole compound 4 to increase the nucleophilicity. Accordingly, it is desirable to use the base having a pKa value larger than that of imidazole compound 4.

In the method for preparing ionic liquid type crown ether of the present invention, ST 3 is the step of reacting the compound 5 prepared in ST 2 with a compound 6 to form crown ether expressed by Chemical Formula 1 in Scheme 1.

In ST 3, after applying heat to the compound 5 and the compound 6, wherein m=n or m≠n, to reflux, the resulting reactant is cooled at room temperature to form ionic liquid type crown ether of symmetrical or asymmetrical on the axis of two imidazolium.

The ranges of the m or n are identical with those in the ionic liquid type crown ether.

In the method for preparing ionic liquid type crown ether of the present invention, ST 4 is the step of preparing ionic liquid type crown ether, wherein the anions are exchanged, expressed by Chemical Formula 1' in Scheme 2, via an anion exchange reaction with the ionic liquid type crown ether of Chemical Formula 1 of Scheme 1 prepared in ST 3. In this case, the X'⁻ may include Lewis base having a negative charge, such as $AlCl_4^-$, $Al_2Cl_7^-$, $BF_4^-$, $PF_6^-$, $SbF_6^-$, $Cl^-$, $Br^-$, $I^-$, $NO_3^-$, $HSO_4^-$, $CF_3COO^-$, $CF_3SO_3^-$, $(CF_3SO_3)_2N^-$, etc.

The anion exchange reaction in ST 4 dissolves the compound of Chemical Formula 1 in deionized water where anion chemical species expressed as the X'⁻ are melted, or in an appropriate solvent, such as THF, acetone, etc., which can dissolve the compound of Chemical Formula 1, and stirs the resulting solution at room temperature for 1 to 30 hours. Next, the phase including the ionic liquid type crown ethers is isolated or the complex in which the ionic liquid type crown ethers are dissolved is filtrated and, then, the resultants are washed by deionized water or the solution in which the anion chemical species expressed as X'⁻ are melted, thus completing the anion exchange reaction.

Furthermore, the present invention provides a method for isolating metal ions including radioactive isotopes using the ionic liquid type crown ether expressed by Chemical Formula 1.

A variety of the cycle sizes of the ionic liquid type crown ether in accordance with the present invention can be prepared suitable for the sizes of metal ions to be isolated by regulating the l, m and n as described in detail above. Accordingly, the metal ions suitable for the cycle size of the ionic liquid type crown ether can be captured and isolated by forming complexes with unshared electron pairs of the crown ether.

The isolatable radioactive isotopes include Sr, Y, Tc, Sm, Ho, Re, etc. Besides, any metal ions harmonized with the cycle size of the ionic liquid type crown ether can be isolated without any limitations.

DETAILED DESCRIPTION OF THE INVENTION

Hereinafter, a detail description of the present invention will be given with reference to the attached drawings. The present invention is not restricted to the following embodiments, and many variations are possible within the spirit and scope of the present invention. The embodiments of the present invention are provided in order to more completely explain the present invention to anyone skilled in the art.

EMBODIMENT

Preparation of Ionic Crown Ether

Ionic liquid type crown ether was prepared via the method for preparing ionic liquid type crown ether in accordance with the present invention.

Embodiment 1

Preparation of cyclo-bis1N,1N'-[(4,7-dioxa)-1,8-octyl]-diimidazolium chloride; [(2,2) O$_{Et}$-Im] [Cl] 10

A target compound 10 was prepared via a reaction expressed by Scheme 3 below in accordance with Embodiment 1 of the present invention.

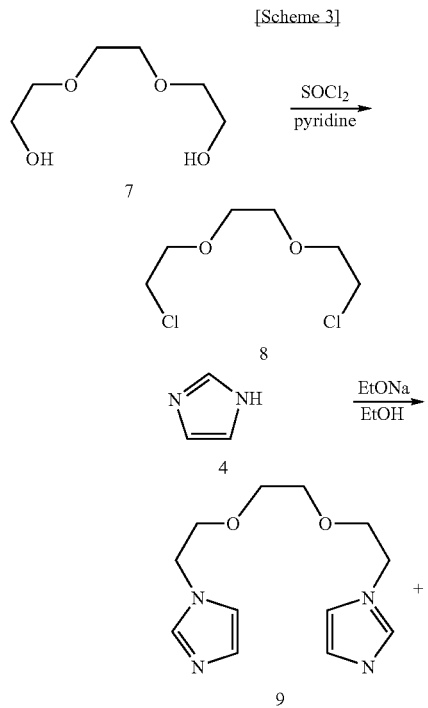

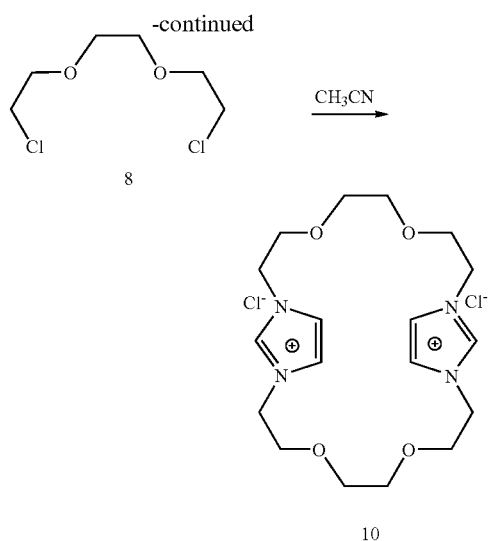

Step 1: Preparation of 1,8-dichloro-3,6-dioxaoctane 8

A target compound 8 (46.2 g, 0.24 mol, 91%) was obtained by reacting triethyleneglycol 7 in benzene solvent with thionylchloride melted in pyridine.

$^1$H NMR (CDCl$_3$): 3.55-3.57(m, 4H, OCH$_2$), 3.60-3.69(m, 4H, OCH$_2$), 3.76(t, 4H ClCH$_2$)

Step 2: Preparation of 1N, 1N'-[(3,6-dioxa)-1,8-octyl]-diimidazole 9

Sodiumethoxide and the compound 8 (18.71 g, 0.10 mol) obtained in Step 1 were added to a solution where imidazole (13.62 g, 0.20 mol) is melted in 100 mL of ethanol. Then, the resultant complex was stirred and heated to reflux till white solids precipitated for six hours. After cooling the complex at room temperature, the solids were filtered and the filtrate was concentrated under reduced pressure and purified by silica gel column chromatography (dichloromethane/methanol=50/50 volume %), thus obtaining a target compound 9 of colorless liquid (22.50 g, 0.089 mmol, 89%).

$^1$H NMR (CDCl$_3$): 3.54-3.56(m, 4H), 3.66(t, 4H, 4.5 Hz), 3.91(t, 4H), 7.98(d, 4H, 1.8 Hz), 9.40(s, 2H, 1.8 Hz)

Step 3: Preparation of cyclo-bis1N,1N'-[1,8-(4,7-dioxa)octyl]-diimidazolium chloride; [(2,2) O$_{Et}$-Im] [Cl] 10

The compound 9 prepared in Step 2 was dissolved in 250 mL of anhydrous acetonitrile, 1 equivalent weight of compound 8 was added to the solution and, then, the resultant solution was heated to reflux for 24 hours. After cooling the complex at room temperature, the cooled complex was concentrated under reduced pressure and purified by silica gel and activated carbon column chromatography (dichloromethane/methanol=50/50 volume %), thus obtaining a target compound 10 of colorless liquid of high viscosity (36.0 g, 0.0689 mol, 78%).

$^1$H NMR (CDCl$_3$): 3.54-3.56(m, 8H), 3.66(t, 4H, 4.5 Hz), 3.92(t, 8H, 4.5 Hz), 7.98(d, 4H, 1.8 Hz), 9.40(s, 2H, 1.8 Hz)

Embodiment 2

Preparation of cyclo-bis1N,1N'-[(3,6,9-trioxa)-1,11-undecyl]-diimidazolium chloride;[(3,3)O$_{Et}$-Im] [Cl] 14

A target compound 14 was prepared via a reaction expressed by Scheme 4 below in accordance with Embodiment 2 of the present invention.

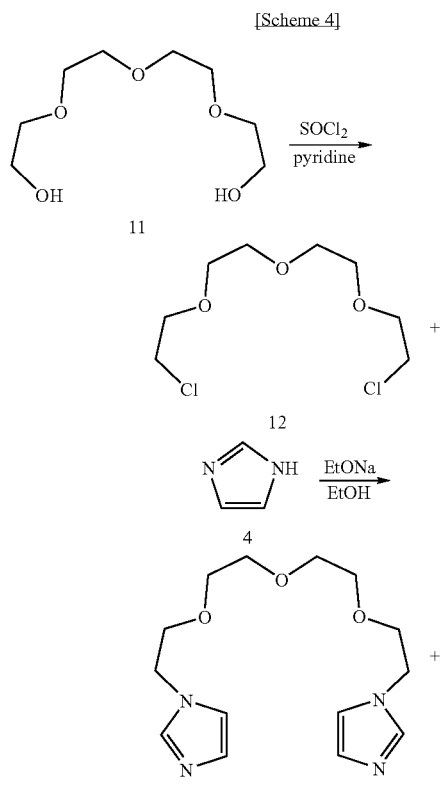

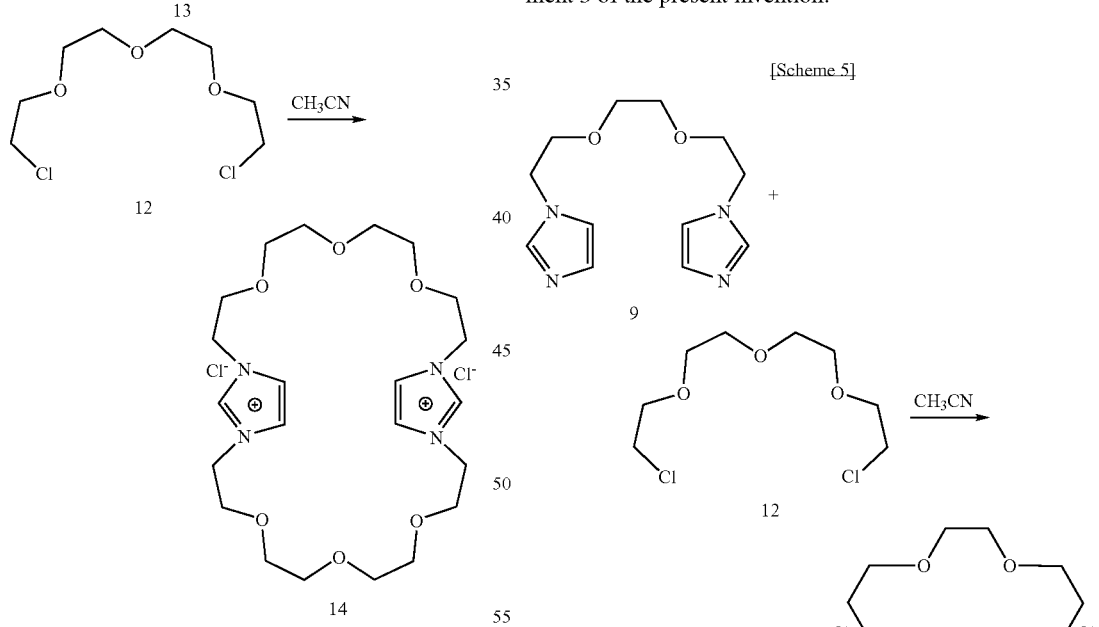

Step 1: Preparation of 1,11-dichloro-3,6,9-trioxaundecane

A target compound 12 (55 g, 0.238 mmol, 84%) was obtained by using tetraethyleneglycol 11, instead of triethyleneglycol 7 used in Step 1 of Embodiment 1, via the same method as Step 1 of Embodiment 1.

bp 65~68° C. (0.1 torr), 112~113° C. (0.8 mmHg);

IR (neat): 1456, 1353, 1300, 1249, 1200, 1105, 851, 666 cm$^{-1}$; and $^1$H NMR (CDCl$_3$): 3.56-3.58(m, 4H), 3.64-3.74(m, 8H), 3.78(t, 4H, 4.5 Hz)

Step 2: Preparation of 1N,1N'-[(3,6,9-trioxa)-1,11-undecyl]-diimidazole 13

A target compound 13 (25 g, 0.085 mol, 85%) was obtained by using the compound 12 prepared in Step 1 of Embodiment 2, instead of the compound 8 used in Step 2 of Embodiment 1, via the same method as Step 2 of Embodiment 1.

$^1$H NMR (CDCl$_3$): 3.57-3.61 (m, 4H), 3.65-3.75 (m, 4H), 3.88(t, 4H, 4.5 Hz), 4.61(t, 4H, 4.6 Hz), 7.99(d, 4H, 1.8 Hz), 9.45(s, 2H, 1.8 Hz)

Step 3: Preparation of cyclo-bi-1N,1N'[(3,6,9-trioxa)-1,11-undecyl]-diimidazolium chloride;[(3,3) O$_{Et}$-Im][Cl] 14

A target compound 14 (39.4 g, 0.0868 mol, 72%) was prepared by using the compounds 12 and 13 obtained in Steps 1 and 2, instead of the compounds 8 and 9 obtained in Step 3 of Embodiment 3, via the same method as Step 3 of Embodiment 1.

$^1$H NMR (CDCl$_3$): 3.53-3.59 (m, 8H), 3.65-3.74 (m, 8H) 3.86(t, 8H, 4.5 Hz), 4.61(t, 8H, 4.5 Hz), 7.92(d, 4H, 1.8 Hz), 9.43(s, 2H, 1.8 Hz)

Embodiment 3

Preparation of cyclo-1N,1N'-[(3,6,9-trioxa)-1,11-undecyl]-3N,3N'-[(3,6-dioxa)-1,8-octyl]-diimidazolium chloride;[(3,2)O$_{Et}$-Im] [Cl] 15

A target compound 15, asymmetrical ionic liquid type crown ether, was prepared using the intermediates, obtained via the reactions expressed by Schemes 1 and 2, via a reaction expressed by Scheme 5 below in accordance with Embodiment 3 of the present invention.

A target compound 15 (21.3 g, 0.443 mol, 81%) was obtained using the compound 9 prepared in Step 2 of Embodiment 1 and the compound 12 formed in Step 1 of Embodiment 2 as starting materials, via the reaction expressed by Scheme 5, the same methods as Step 3 of Embodiments 1 and 2.

$^1$H NMR (CDCl$_3$): 3.48-4.01(m, 20H), 4.61(t, 8H, 4.5 Hz), 7.91(d, 4H, 1.8 Hz), 9.41(s, 2H, 1.8 Hz)

Embodiment 4

Preparation of cyclo-1N,1N'-[(3,6,9,11-tetraoxa)-1,14-tetradecyl]-3N,3N'-[(3,6,9-trioxa)-1,11-undecyl]-diimidazolium chloride;[(4,3)O$_{Et}$-Im][Cl] 17

A target compound 17 (15.8 g, 0.27 mol, 64.6%), asymmetrical ionic liquid type crown ether, was prepared using the compounds 13 and 16 via a reaction expressed by Scheme 6 below, the same method as Embodiment 3.

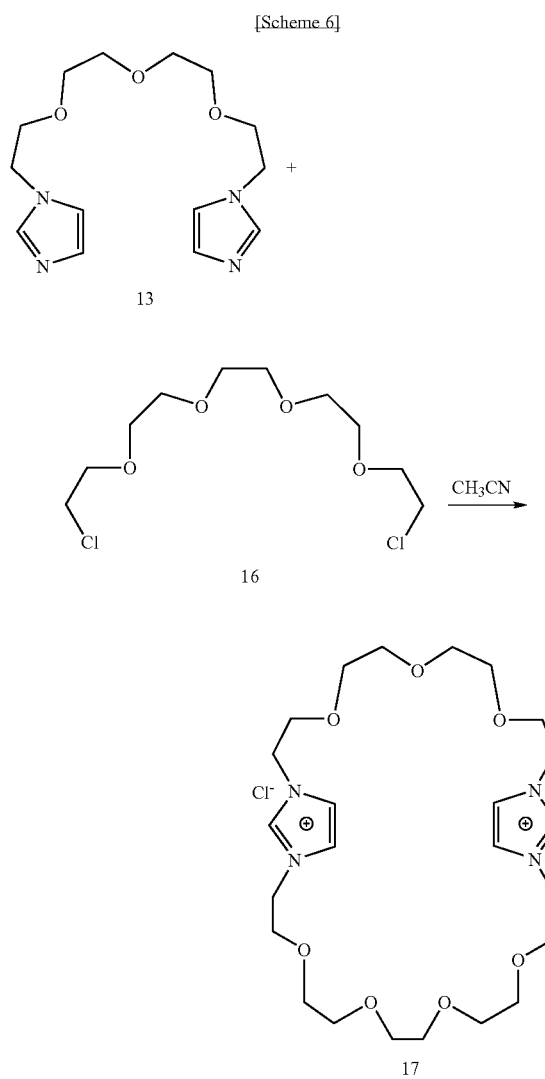

$^1$H NMR (CDCl$_3$): 3.31-3.40(m, 28H), 4.58(t, 8H, 4.5 Hz), 7.91(d, 4H, 1.8 Hz), 9.42(s, 2H, 1.8 Hz)

Embodiment 5

Preparation of cyclo-bis1N,1N'-[(4,7-dioxa)-1,8-octyl]-dimidazolium chloride; [(2,2) O$_{Et}$-Im] [PF$_8$] 18

After melting the ionic liquid type crown ether compound 10 obtained in Embodiment 1 and 2.2 equivalent weights of KPF$_6$ in deionized water, the resultant solution was stirred at room temperature for above two hours and, then, the phases of the solution were separated. Subsequently, the subnatant was dissolved in dichloromethane and the resultant solution was washed by deionized water twice. Last, the solution was concentrated under reduced pressure to obtain a target compound 18 (89%), in which PF$_6^-$ ions were exchanged, as expressed by Scheme 7 below.

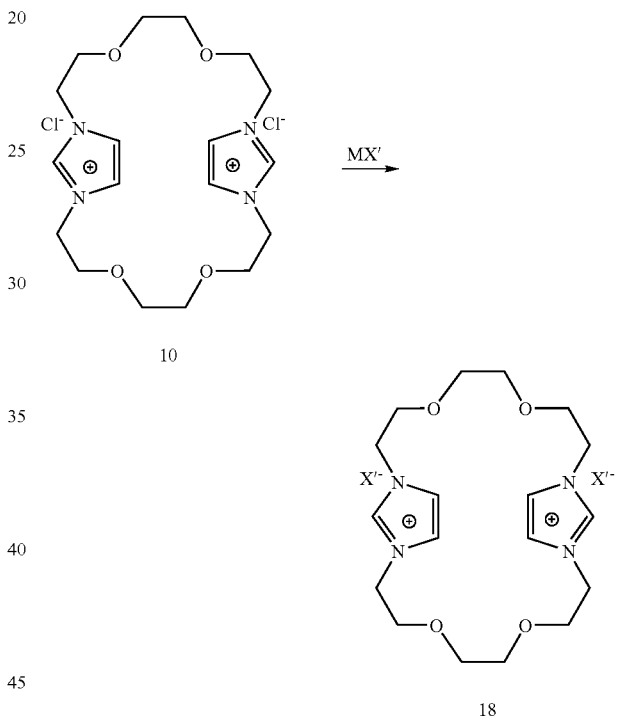

wherein MX' denotes KPF$_6$ and XÅ represents PF$_6^-$.

$_1$H NMR (CDCl$^3$): 3.54-3.60(m, 8H), 3.65-3.73(m, 8H), 3.86(t, 8H, 4.5 Hz), 4.60(t, 8H, 4.5 Hz), 7.92(d, 4H, 1.8 Hz), 9.43(s, 2H, 1.8 Hz)

mass m/z 366.1 (M-BF$_6$)

Embodiment 6

Preparation of cyclo-bis1N,1N'-[(4,7-dioxa)-1,6-octyl]-diimidazolium chloride; [(2,2) O$_{Et}$-Im] [CF$_3$COO] 18

The ionic liquid type crown ether compound 10 obtained in Embodiment 1 was melted in acetone and 2.2 equivalent weights of CF$_6$COONa was added to the solution. The resultant solution was stirred at room temperature for 24 hours and, then, the complex was filtered and washed by acetone twice, thus collecting the filtrate. Subsequently, MgSO$_4$ was added to the organic layer thereof and the resultant organic layer was dried and filtered. Last, the resultant filtrate was concentrated under reduced pressure to obtain a target compound 18 (91%), in which Cl⁻ ions were exchanged into $CF_3COO^-$ ions.

$^1$H NMR (CDCl$_3$): 3.53-3.59(m, 8H), 3.65-3.73(m, 8H), 3.85(t, 8H, 4.5 Hz), 4.60(t, 8H, 4.5 Hz), 7.91(d, 4H, 1.8 Hz), 9.41(s, 2H, 1.8 Hz)

mass: m/z 366.1 (M-CF$_3$COO)

EXPERIMENTAL EXAMPLE

Absorption and Isolation of Metal Ions

The following experiments were carried out to identify absorption and isolation efficiencies of the ionic liquid type crown ether prepared by the present invention.

Experimental Example 1

Absorption and isolation of $^{85}$Sr ions

The ionic liquid type crown ether prepared in Embodiments 1 to 4 was mixed with 1 mL of deionized H$_2$O. The resultant solution was stirred for two minutes and centrifuged by a centrifuge of 2,500 rpm for two minutes. $^{85}$Sr ions (0.005 μCi, 5 μL) were added to the respective ionic liquid type crown ether complexes. Subsequently, the resultant complexes were stirred again for two minutes to mix the two phases sufficiently and, then, centrifuged for two minutes. Each 100 μL of samples was collected from the separated two phases and subjected to measure radioactivity by means of a multi-channel analyzer (HPGe detector coupled to multi-channel analyzer, ORTEC, Oak Ridge, Tenn., USA) and the results were shown in Table 1 below.

TABLE 1

| | Absorption Rate (bp) of $^{85}$Sr | |
|---|---|---|
| IL-CE | Water layer | IL-CE layer |
| Embodiment 1 | 290 | 62 |
| Embodiment 2 | 323 | No detected |
| Embodiment 3 | 170 | 296 |
| Embodiment 4 | 369 | No detected |

As shown in Table 1, it was found that the absorption and isolation efficiencies of $^{85}$Sr ions by [(3,2) O$_{Et}$-Im] [Cl] of Embodiment 3 were very high. The amount of radioactivity of IL-CE layer of Embodiment 1, of which the cycle size was relatively small, was detected smaller than that of IL-CE of Embodiment 3. Meanwhile, no radioactivity was detected in the IL-CE layers of Embodiments 2 and 4, of which the cycle sizes were relatively larger. Accordingly, it could be known that the $^{85}$Sr ions could be selectively captured by [(3,2)O$_{Et}$-Im] [Cl] of Embodiment 3.

Experimental Example 2

Absorption and Isolation of $^{89}$Sr or $^{90}$Sr ions

Using $^{89}$Sr or $^{90}$Sr ions instead of $^{85}$Sr ions of Experimental Example 1, an experiment was carried out to identify the absorption and isolation of the ionic liquid type crown ether prepared in Embodiments 1 to 4 via the same method as Experimental Example 1, and the results were depicted in Table 2 below.

TABLE 2

| | $^{89}$Sr: Absorption Rate (bp) | | $^{90}$Sr: Absorption Rate (bp) | |
|---|---|---|---|---|
| IL-CE | Water layer | IL-CE layer | Water layer | IL-CE layer |
| Embodiment 1 | 292 | 60 | 288 | 63 |
| Embodiment 2 | 312 | No detected | 315 | No detected |
| Embodiment 3 | 173 | 301 | 171 | 295 |
| Embodiment 4 | 370 | No detected | 375 | No-detected |

As depicted in Table 2, it was understood that the results were similar to those of Experimental Example 1 since the volumes of $^{85}$Sr and its isotopes $^{89}$Sr or $^{90}$Sr were alike. That is, it was found that the absorption and isolation efficiencies of [(3,2)O$_{Et}$-Im] [Cl] of Embodiment 3 were most excellent. However, a few or no radioactivity was detected from the $^{89}$Sr or $^{90}$Sr by the IL-CE layer of Embodiment 1, of which the cycle size was relatively small and by the IL-CE layers of Embodiments 2 and 4, of which cycle sizes were relatively large. Accordingly, it could be known that the $^{89}$Sr or $^{90}$Sr ions could be selectively captured by [(3,2)O$_{Et}$-Im] [Cl] of Embodiment 3.

Experimental Example 3

Absorption and Isolation of $^{99m}$Tc ions

The ionic liquid type crown ether prepared in Embodiments 1 to 4 was mixed with 1 mL of deionized H$_2$O. The resultant solution was stirred for two minutes and centrifuged by a centrifuge of 2,500 rpm for two minutes. $^{99m}$Tc ions (2.5 mCi, 1 mL) was added to the respective ionic liquid type crown ether complexes. Subsequently, the resultant complexes were stirred again for two minutes to mix the two phases sufficiently and, then, centrifuged for two minutes. Each 200 μL of samples was collected from the separated two phases and subjected to measure radioactivity by means of a multi-channel analyzer (HPGe detector coupled to multi-channel analyzer, ORTEC, Oak Ridge, Tenn., USA) and the results were shown in Table 3 below.

TABLE 3

| | Absorption Rate (bp) of $^{99m}$Tc | |
|---|---|---|
| IL-CE | Water layer | IL-CE layer |
| Embodiment 1 | 43,017 | 318,365 |
| Embodiment 2 | 105,913 | 318,323 |
| Embodiment 3 | 63,988 | 397,091 |
| Embodiment 4 | 184,215 | 150,395 |

In view of the results shown in Table 3, the absorption rates of $^{99m}$Tc by the IL-CE layers of Embodiment 1 to 4 were detected in sequential order of 86%, 75%, 86% and 45%. From the results, it could be understood that the $^{99m}$Tc could be caught efficiently by the IL-CE layers of [(2,2)O$_{Et}$-Im] [Cl] of Embodiment 1 or [(3,2)O$_{Et}$-Im] [Cl] of Embodiment 3.

Experimental Example 4

Absorption and Isolation of $^{188}$Re ions

Using $^{188}$Re ions, a species of radioactive isotope, an experiment for identifying the absorption and isolation effects was executed via the same method as Experimental Example 1 and the results were depicted in Table 4 below.

TABLE 4

| IL-CE | Absorption Rate (bp) of $^{188}$Re | |
|---|---|---|
| | Water layer | IL-CE layer |
| Embodiment 1 | 179,328 | 180,915 |
| Embodiment 2 | 65,232 | 421,125 |
| Embodiment 3 | 51,250 | 352,362 |
| Embodiment 4 | 99,112 | 319,554 |

In view of the results depicted in Table 4, the absorption rates of $^{188}$Re by the IL-CE layers of Embodiment 1 to 4 were detected in sequential order of 50.2%, 87%, 87% and 76%. From the results, it could be understood that the $^{88}$Re could be seized efficiently by the IL-CE layers of [(3,3) $O_{Et}$-Im] [Cl] of Embodiment 2 or [(3,2) $O_{Et}$-Im] [Cl] of Embodiment 3.

Consequently, the present invention can provide the ionic liquid type crown ether and isolate metal ions including radioactive isotopes efficiently using the same. Furthermore, the prevent invention provides crown ether valuably used as a recyclable and environment-friendly isolating medium by preparing crown ether of ionic liquid type.

What is claimed is:

1. An ionic liquid type crown ether derivative represented by Chemical Formula 1 below:

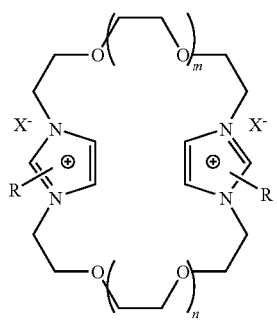

[Chemical Formula 1]

wherein m and n are independently a positive integer from 1 to 4;

X⁻ represents an anion chemical species of ionic liquid; and

R expresses hydrogen or an alkyl group of $C_1$~$C_6$.

2. The ionic liquid type crown ether derivative as recited in claim 1, wherein m and n is positive numbers of 1 to 3;

anion chemical species of ionic liquid is one selected from the group consisting of $AlCl_4^-$, $Al_2Cl_7^-$, $BF_4^-$, $PF_6^-$, $SbF_6^-$, $Cl^-$, $Br^-$, $I^-$, $NO_3^-$, $HSO_4^-$, $CF_3COO^-$, $CF_3SO_3$ and $(CF_3SO_3)_2N^-$; and R is hydrogen.

3. A method for preparing an ionic liquid type crown ether derivative of claim 1, comprising:

substituting alcohol groups of an ethyleneglycol compound 2 with X⁻s to form a compound 3 [ST 1];

reacting the compound 3 prepared in ST 1 with substituted or non-substituted imidazoles compound 4 to prepare a compound 5, wherein the Xs of the compound 3 are substituted with the imidazole of compounds 4 [ST 2]; and reacting the compound 5 prepared in ST 2 with a compound 6 to form an ionic liquid type crown ether represented by Chemical Formula 1 [ST 3].

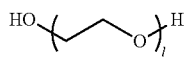

[Compound 2]

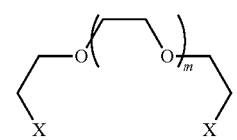

[Cpmpound 3]

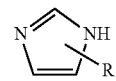

[Compound 4]

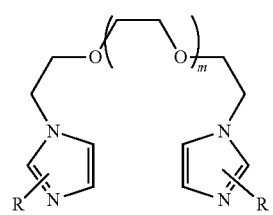

[Compound 5]

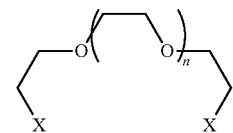

[Compound 6]

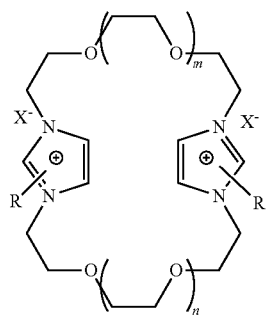

[Chemical Formula 1]

wherein m, n, X⁻, and R are as defined in claims 1, and 1 is a positive integer from 3 to 6.

4. The method as recited in claim 3 further comprising:

carrying out an anion exchange reaction of the ionic liquid type crown ether, prepared in ST 3, of Chemical Formula 1 with X'⁻, to prepare an ionic liquid type crown ether represented by Chemical Formula 1' having different physical properties [ST 4]:

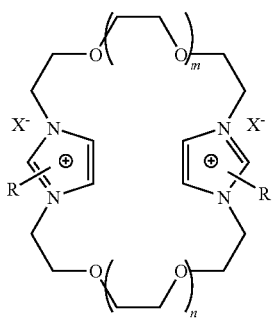

[Chemical Formula 1]

wherein m, n, 1, $X^-$, and R are as defined in claim 3; and $X'^-$ is one anion chemical species selected from the group consisting of $AlCl_4^-$, $Al_2Cl_7^-$, $BF_4^-$, $PF_6^-$, $SbF^-$, $Cl^-$, $Br^-$, $I^-$, $NO_3^-$, $HSO_4^-$, $CF_3COO^-$, $CF_3SO_3^-$ and $(CF_3SO_3)_2N^-$.

5. The method as recited in claim 3, wherein in ST 2 the compound 3 prepared in ST 1 is reacted with the imidazole compound 4 at room temperature for five to seven hours, after increasing nucleophilicity of the imidazole compound 4 under basic condition.

6. The method as recited in claim 3, wherein in ST 3 the compound 5 prepared in ST 2 and the compound 6 having the same m as the compound 5 or having different n from compound 5 are heated to reflux over 24 hours and the resulting reactant is cooled at room temperature to form symmetrical or asymmetrical ionic liquid type crown ether based on the imidazole.

7. A method for isolating a metal ion or a radioactive isotope by cycle sizes of a compound expressed by Chemical Formula 1 in claim 1 comprising:

i) forming a complex by stirring an aqueous solution of a metal ion or a radioactive isotope with a compound expressed by Chemical Formula 1 in claim 1;

ii) separating layers of aqueous solution and the complex formed in step i) by centrifugation; and iii) isolating a metal ion or a radioactive isotope.

8. The method as recited in claim 7, wherein the radioactive isotope is selected from the group consisting of Sr, Y, Tc, Sm, Ho and Re.

9. The ionic liquid type crown ether derivative as recited in claim 2, wherein, m and n are 1; and anion chemical species of ionic liquid is $Cl^{31}$.

10. The method as recited in claim 4, wherein the anion exchange reaction in ST 4 comprises:

(i) dissolving an anion chemical species represented as $X'^-$ in a solvent selected from the group consisting of deionized water, THF, and acetone;

(ii) adding a compound of Chemical Formula 1 to the solution of $X'^-$ prepared in step (i);

(iii) stirring the resulting solution of $X'^-$ and the compound of Chemical Formula 1 prepared in step (ii) at room temperature for 1 to 30 hours; and (iv) filtering the mixture resulting from step (iii) and removing solvent from filtrate to obtain a compound represented by Chemical Formula 1'.

* * * * *